United States Patent [19]

Klein

[11] 4,394,378

[45] Jul. 19, 1983

[54] 3-(TRIMETHOXYSILYL) PROPYLDIDECYLMETHYL AMMONIUM SALTS AND METHOD OF INHIBITING GROWTH OF MICROORGANISMS THEREWITH

[76] Inventor: Stewart E. Klein, Richardson La., Harrison, N.Y. 10528

[21] Appl. No.: 281,319

[22] Filed: Jul. 8, 1981

[51] Int. Cl.³ .......................... C07F 7/10; A61L 13/00
[52] U.S. Cl. ..................................... 424/184; 556/413; 71/67; 71/121
[58] Field of Search ..................... 556/413; 71/67, 121; 424/184

[56] References Cited

U.S. PATENT DOCUMENTS

| | | | |
|---|---|---|---|
| 3,560,385 | 2/1971 | Roth | 556/413 UX |
| 3,661,963 | 5/1972 | Pepe et al. | 556/413 |
| 3,794,736 | 2/1974 | Abbott et al. | 556/413 X |
| 3,817,739 | 6/1974 | Abbott et al. | 556/413 X |
| 4,005,025 | 1/1977 | Kinstedt | 556/413 UX |
| 4,282,366 | 8/1981 | Eudy | 556/413 |

*Primary Examiner*—Paul F. Shaver
*Attorney, Agent, or Firm*—Hubbell, Cohen, Stiefel & Gross

[57] ABSTRACT

The growth of bacteria, fungi or the like is inhibited by contacting such microorganisms with an effective amount of certain silyl quaternary ammonium salts, e.g., 3-(trimethoxysilyl) propyldidecylmethyl ammonium chloride.

9 Claims, No Drawings

3-(TRIMETHOXYSILYL) PROPYLDIDECYLMETHYL AMMONIUM SALTS AND METHOD OF INHIBITING GROWTH OF MICROORGANISMS THEREWITH

TECHNICAL FIELD

The present invention relates to certain silyl quaternary ammonium salts and a method of inhibiting the growth of bacteria and fungi therewith. In particular, the invention relates to the use of such salts as bactericidal or fungicidal agents on textiles or other substrates.

BACKGROUND ART

It is well known in the art that organosilicon quaternary ammonium compounds possess bacteriostatic, fungistatic and algaestatic and/or bactericidal, fungicidal and algaecidal properties. See, for example, U.S. Pat. Nos. 3,560,385; 3,730,701; 3,794,736; 3,817,739; 3,865,728; and 4,005,025; and British Patent No. 1,386,876. Thus, U.S. Pat. No. 3,730,701 discloses a variety of silyl quaternary ammonium compounds having a single long chain alkyl radical of from 11 to 22 carbon atoms. For example, one such compound, 3-(trimethoxysilyl)propyl octadecyldimethyl ammonium chloride is a commercial antimicrobial product marketed by Dow Corning as "Bioguard Q 9-5700" (EPA No. 34292-1). U.S. Pat. No. 3,794,736 describes a number of other organosilicon amines and salts thereof exhibiting antimicrobial activity against a wide variety of organisms.

In accordance with this invention there are provided a number of silyl quaternary ammonium salts which have equal or greater antimicrobial activity than the previously known compounds.

DISCLOSURE OF INVENTION

The present invention relates to certain silyl quaternary ammonium salts, particularly 3-(trimethoxysilyl)propyldidecylmethyl ammonium salts, e.g., the fluoride, chloride, bromide, iodide, sulfate and acetate thereof, and their use as fungicides and bactericides on a variety of substances having reactive surfaces, particularly textile fabrics and fibers. As used herein, the term "substances having reactive surfaces" or "surface reactive substrate(s)" is meant to include any material whose surface is able to form covalent chemical bonds with the didecylmethyl-substituted silyl quaternary ammonium compounds of the invention. It has now been found that these didecylmethyl substituted ammonium compounds more effectively inhibit the growth of such microorganisms, including, for example, both various gram-positive and gram-negative bacteria, than their known adjacent homologs.

While the specific site of action of the organo-silicon quaternary ammonium compounds is still under investigation it is known that the compounds are chemically bonded to a variety of reactive surfaces and are not removed therefrom by repeated leaching or washing with water. Thus, the compounds of the present invention are useful to impart durable bioactive properties to surfaces like natural and synthetic textile fibers, siliceous materials like glass, stone and ceramics; metals; and also, leather, wood, plastic and the like. Generally, the surface reactive materials are treated by contacting the same with the bioactive compound, e.g., by either dipping, spraying, padding, or brushing the compound of the present invention onto the substrates either prior to infestation by microorganisms to prevent the growth thereof, or after infestation to kill and to prevent new growth thereof.

The compounds of the present invention are active in solution as well as when applied to solid surfaces. The antimicrobial compounds may thus be employed as the pure compounds, in aqueous solution or dispersion, or in organic solvent media.

Preferably, the compounds of the present invention are dissolved in a suitable organic water miscible solvent forming a solution containing about 50% of the compound of the present invention as active ingredient.

BEST MODE FOR CARRYING OUT THE INVENTION

In accordance with the present invention it has been found that 3-(trimethoxysilyl)propyldidecylmethyl ammonium salts exhibit antimicrobial properties which are superior to those of their known adjacent homologs. Such materials are thus useful for a variety of bactericidal, fungicidal and the like applications for which the use of silyl quaternary ammonium compounds has previously been proposed.

The compounds of the present invention may be prepared by known methods. Thus, the tertiary amine, i.e., didecylmethyl amine, is reacted with an appropriate silane, e.g., 3-chloropropyltrimethoxysilane with or without the presence of a suitable solvent such as methanol. The alkylation reaction of the tertiary amine proceeds smoothly resulting in the production of 3-(trimethoxysilyl)propyldidecylmethyl ammonium chloride. Of course, other silanes may be similarly reacted to form other quaternary ammonium halides, e.g., the fluoride, bromide, or iodide, within the scope of the invention. Similarly, silanes incorporating sulfate or acetate anions may be converted to the corresponding quaternary ammonium salts, within the purview hereof.

Alternatively, the salts of the present invention may be prepared by reacting didecylamines with the trimethoxysilylpropylhalide, sulfate or acetate in the presence of sodium methylate to yield the corresponding tertiary amines which are subsequently methylated to form the organosilicon quaternary ammonium salts. A further method for preparing the compound of the present invention includes the preparation of the allyldidecylamine, followed by hydrosilylation thereof with trimethoxysilane to produce 3-(didecylamino)propyltrimethoxysilane, which is then treated with an appropriate methyl halide to yield the compound of the present invention.

The preferred compound, 3-(trimethoxysilyl)propyldidecylmethyl ammonium chloride, may directly contact the surface of the material to be treated by either spraying or brushing, or the surface reactive substrate may be immersed in the pure antimicrobial compound or in a solution thereof in an appropriate solvent.

Surface reactive materials or substrates to which the compound of the invention can be chemically bonded include siliceous materials and metallic surfaces. Leather, wood, rubber and plastic have also been shown to have reactive surfaces. Indeed, the preferred class of substrates having reactive surfaces to which the compound of the invention can readily bond comprises the natural and synthetic textile fibers and the corresponding fabrics thereof. Such natural fibers include cotton, wool, linen and felt; similarly bondable synthetic fibers include those comprised wholly of synthetic polymeric material such as viscose, cellulose acetate or triacetate; or nylons, polyether, vinyl polymers, including polyolefins, acrylics and modacrylics or the like; or blends of such materials with natural fibers.

Suitable solvents in which the compound of the invention may be dissolved for bactericidal, fungicidal or similar applications include water and organic water miscible solvents like alcohols, such as methanol, ethanol and butanol; methyl Cellosolve and ethyl Cellosolve; ketones, such as methylethyl ketone. For textile treatment, solvents used in commercial dry cleaning processes, such as hydrocarbons, chlorinated hydrocarbons, ethers and benzene may alternatively be used.

As disclosed hereinabove, the active compound of the present invention may be applied to a variety of surfaces by any suitable means. For example, it is possible to spray the antimicrobial compound into shoes to inhibit or prevent growth of microorganisms therein. The pure compound or a solution thereof may also be applied to walls to prevent mold and mildew, or may be added to fillers used in paints to prepare paints with antimicrobial properties. For treating textiles, the compound may be dispersed in the solvents used in commercial dry cleaning processes and thus be readily brought into contact with textiles to be treated. Alternatively, the active compound may be applied to textile fabrics or fibers by exhaustion techniques, involving the use of closed systems in which the fibers or fabrics to be treated are immersed in a treating bath under preferably slightly elevated temperature conditions to effect absorption and fixation of the bioactive compound on the textile fibers and thus "exhaust" the same from the bath. Such techniques are more fully described, for example, in my prior U.S. Pat. No. 3,788,803.

Another preferred method for applying the bioactive compound of the present invention to fabrics or textile fibers is by padding. The fabric to be treated may be immersed in a trough or padder containing a solution of the antimicrobial compound. The concentration of the active ingredient in the solution is adjusted depending upon the ability of the substrate to pick up the antimicrobial compound from the bath. Of course, finishing agents such as a softening agent or the like may be added to either the exhaustion or the padding bath.

Thus, in the preferred embodiments of the present invention for applying the antimicrobial compound of the invention to textile fibers or fabrics, the fibers or fabrics are immersed in a bath containing the compound (in pure or dissolved form) for a period of from about 3-5 minutes to about 20-30 minutes at temperatures of from about 25° to 95° C., and preferably from about 40° to 70° C. The amount of bioactive compound thus bonded to the textile fibers may vary, depending on the solvent and the particular structure of the textile employed. The active ingredient may be applied in an amount of from about 0.1% to 1.0% by weight of a textile substrate. Upon removal of the textile fibers from such an exhaustion or padding bath, the treated material may be dried in accordance with conventional practice in the art, thereafter woven, knitted, or otherwise converted to piece goods (if treated in fibrous form), and subjected to conventional finishing operations.

In the following examples all parts and percentages are by weight, and all temperatures in degrees Celsius, unless otherwise indicated.

EXAMPLE 1

Preparation of
3-(Trimethyoxysilyl)propyldidecylmethyl Ammonium Chloride

In a 12-liter 3-neck round bottom reaction flask equipped with stirrer, thermometer and condenser was placed 4746 grams (15.2 moles) of didecylmethylamine and 3160.7 grams (15.9 moles) 3-chloropropyltrimethoxysilane. The solution was stirred with heating at 110° C. under a nitrogen atmosphere for 48 hours. The dark yellow/orange liquid was then placed under vacuum (5 torr), and approximately 135 mls. residual 3-chloropropyltrimethoxysilane was removed. The remaining product was then added slowly to 7750 grams of methanol with stirring to produce a product containing 50% active material.

Reaction with other, appropriately substituted propyltrimethoxysilanes gives other salts of the desired silyl quaternary ammonium compound, e.g., the bromides or iodides thereof.

EXAMPLE 2

Preparation of
3-(Trimethoxysilyl)Propyldidecylmethyl Ammonium Chloride In Methanol In a 2-liter single-neck preparation flask was placed 804 grams (2.58 moles) of didecylmethylamine, 536.5 grams (2.7 moles) of 3-chloropropyltrimethoxysilane and 4500 grams anhydrous methanol. The reaction mixture was stirred with heating to a gentle reflux under nitrogen for 48 hours. The reaction was cooled to 35° C. and 890 grams of anhydrous methanol was added. The resulting yellow/orange solution contained 50 wt. % active material.

EXAMPLE 3

Comparison of Antibacterial Activity of
3-(Trimethoxysilyl)propyldidecylmethyl Ammonium Chloride With The Activity Of Other Di-Long Chain Alkyl Substituted Organo Silicon Quaternary Ammonium Compounds Against Gram Positive and Gram Negative Bacteria The activity of the compound of Example 1 was compared with various higher and lower adjacent homologs against a gram positive (*Staph aureus* ATCC 6538) and gram negative (*Klebsiella pneumoniae* ATCC 4352) strain.

10 ml of a 10% aqueous solution of each bactericide tested was prepared. For serial dilutions were made by pipeting 1 ml of each 10% solution into a 10 ml volumetric flask and filling to the mark with water. 0.1 ml of each serial dilution was added to 9.9 ml of sterile molten nutrient agar in tubes which were maintained at 47° C. in a water bath. 0.1 ml of blank water was added to 9.9 ml of sterile molten nutrient agar to serve as a control. 0.1 ml aliquots of a 24 hour culture of each test organism were pipeted into six sterile petri dishes previously labeled 1000, 100, 10, 1 and 0.1 and control organism. The contents of each tube was then poured into its respective petri dish, swirled and allowed to solidify. The petri dishes were incubated, inverted, for 48 hours at 37° C. The results were as follows:

TABLE I

| | Gram Positive Organism Staph Aureus | | Gram Negative Organism K. Pneumoniae | |
|---|---|---|---|---|
| Compounds | 100 ppm | 1000 ppm | 100 ppm. | 1000 ppm |
| Example 1 | NG[1] | NG | NG | NG |
| Control A[3] | G[2] | NG | G | NG |
| Control B[4] | G | G | G | G |
| Control C[5] | G | G | G | G |

[1] NG = No growth
[2] G = Growth
[3] 3-(trimethoxysilyl)propyldioctylmethyl ammonium chloride
[4] 3-(trimethoxysilyl)propyldidodecylmethyl ammonium chloride
[5] 3-(trimethoxysilyl)propyldihexadecylmethyl ammonium chloride.

The compound of Example 1 prevented growth of the test bacteria at concentrations of 100 ppm of the test compound, while the higher and lower homologs thereof were unable to prevent bacteria growth at that concentration.

EXAMPLE 4

Comparison of Antibacterial Activity of 3-(Trimethoxysilyl)propyl didecylmethyl Ammonium Chloride With The Activity of Mono-Long Chain Alkyl Substituted Organo-Silicon Quaternary Ammonium Compounds Against Gram Positive and Gram Negative Bacteria The compound of Example 1 was also compared with related compounds having only one long chain alkyl radical. The test was conducted according to the procedure of Example 1. The following results were obtained:

TABLE II

| Compounds | Staph aureus (ATCC 6528) (ppm) | K. pneumoniae (ATCC 4352) (ppm) | E. coli (ATCC 11229) (ppm) | Pseud. aeruginosa (QM 1468) (ppm) |
|---|---|---|---|---|
| Example 1 | 100 | 100 | >4200 | >4200 |
| Control D[6] | 100 | 100 | >4200 | >4200 |
| Control E[7] | 100 | >4200 | >4200 | >4200 |

[6] 3-(trimethoxysilyl)propyldecyldimethyl ammonium chloride
[7] 3-(trimethoxysilyl)propyloctadecyldimethyl ammonium chloride commercially marketed as "Bioguard Q 9-5700" (EPA No. 3492-1) by Dow Corning.

The activity of the compound of Example 1 was as great as that of the mono-long chain substituted compound Control D. The compound of Example 1 exhibited antimicrobial activity against the tested gram positive strain similar to that of the commercial product (Control E), but showed greater activity than the commercial product against the tested gram negative strain Klebsiella pneumoniae. When the compounds of Example 1 and Control E were applied to polyester fabric, similar results were obtained against K. pneumoniae bacteria at concentrations of 0.25 to 0.5% active ingredient by weight of fabric while on 100% cotton fabric at concentration levels of 0.25 to 1.0% active ingredient by weight of fabric the compound of Example 1 again exhibited greater activity against K. pneumoniae than the commercial product (Control E).

From the preceding it may be seen that in accordance with the present invention new organosilicon quaternary ammonium salts are provided which have improved bactericidal, fungicidal and similar antimicrobial activities, and which may be applied to a variety of surface active materials. It should be understood that the preferred embodiments described above are for illustrative purposes only and are not to be construed as limiting the scope of the invention which is properly delineated in the appended claims.

I claim:

1. A silyl quaternary ammonium compound having the formula

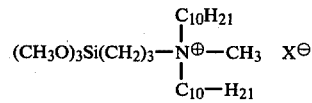

wherein X is selected from the group consisting of fluoride, chloride, bromide, iodide, sulfate and acetate.

2. 3-(trimethoxysilyl)propyldidecylmethyl ammonium chloride.

3. A method of inhibiting the growth of Staph aureus and/or K. pneumoniae on surface reactive substrates by contacting said organisms with a silyl quaternary ammonium compound of the formula

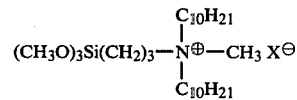

wherein X is selected from the group consisting of fluoride, chloride, bromide, iodide, sulfate and acetate, in an amount effective to inhibit the growth of said organisms.

4. The method of claim 3, wherein the quaternary ammonium compound is 3-(trimethoxysilyl)propyldidecylmethyl ammonium chloride.

5. The method of claim 3 wherein said substrate is a siliceous material.

6. The method of claim 3 wherein said substrate is a metal.

7. The method of claim 3 wherein said substrate is selected from the group consisting of leather, wood, rubber and plastic.

8. The method of claim 3 wherein said substrate is made of natural or synthetic textile fibers.

9. The method of claim 8 wherein the quaternary compound is employed in an amount of from 0.1 to 1.0% by weight of said textile substrate.

* * * * *